United States Patent
Zhai et al.

(10) Patent No.: US 8,653,310 B2
(45) Date of Patent: Feb. 18, 2014

(54) PROCESS FOR MAKING CIS-1-CHLORO-3,3,3-TRIFLUOROPROPENE

(71) Applicant: Honeywell International Inc., Morristown, NJ (US)

(72) Inventors: Yian Zhai, Amherst, NY (US); Andrew Joseph Poss, Kenmore, NY (US); Rajiv Ratna Singh, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 13/674,177

(22) Filed: Nov. 12, 2012

(65) Prior Publication Data

US 2013/0150633 A1  Jun. 13, 2013

Related U.S. Application Data

(60) Provisional application No. 61/567,665, filed on Dec. 7, 2011.

(51) Int. Cl.
*C07C 17/10* (2006.01)

(52) U.S. Cl.
USPC .......................................... 570/154

(58) Field of Classification Search
None
See application file for complete search history.

(56) References Cited

U.S. PATENT DOCUMENTS

| | | | |
|---|---|---|---|
| 5,616,819 | A | 4/1997 | Boyce et al. |
| 5,710,352 | A | 1/1998 | Tung |
| 6,111,150 | A | 8/2000 | Sakyu et al. |
| 6,362,383 | B1 | 3/2002 | Wilmet et al. |
| 6,844,475 | B1 | 1/2005 | Tung et al. |
| 6,958,424 | B1 | 10/2005 | Nair et al. |
| 7,829,747 | B2 | 11/2010 | Wang et al. |
| 2008/0103342 | A1 | 5/2008 | Wang et al. |
| 2010/0145112 | A1 | 6/2010 | Ishihara et al. |
| 2011/0201853 | A1 | 8/2011 | Tung et al. |
| 2012/0215041 | A1 | 8/2012 | Nair et al. |

FOREIGN PATENT DOCUMENTS

| | | | |
|---|---|---|---|
| WO | WO 2010016401 A2 * | 2/2010 | |
| WO | 2010059496 A1 | 5/2010 | |
| WO | 2010068715 A2 | 6/2010 | |

OTHER PUBLICATIONS

PCT ISR & Written Opinion issued in PCT/US2012/066768 dated Mar. 13, 2013.
J. Am. Chem. Soc., 64 (1942) 1157-9.

* cited by examiner

*Primary Examiner* — Johann R Richter
*Assistant Examiner* — Medhanit Bahta
(74) *Attorney, Agent, or Firm* — Erika S. Wilson

(57) ABSTRACT

Disclosed is a process for making cis-1-chloro-3,3,3-trifluoropropene comprising reacting 3,3,3-trifluoropropyne with HCl in a reaction vessel at a yield of at least about 80%.

26 Claims, No Drawings

PROCESS FOR MAKING CIS-1-CHLORO-3,3,3-TRIFLUOROPROPENE

CROSS-REFERENCE TO RELATED APPLICATION

This application claims domestic priority to commonly owned, U.S. Provisional Patent Application Ser. No. 61/567,665, filed Dec. 7, 2011, the disclosure of which is hereby incorporated herein by reference.

FIELD OF THE INVENTION

This invention relates to the preparation of hydrochlorofluoroolefins (HCFOs) which have negligible ozone depletion potential (ODP) and low global warming potential (GWP) and are suitable for use in applications such as blowing agents and solvents. More particularly, this invention relates to a processes for making the compound, cis-1-chloro-3,3,3-trifluoropropene. This compound has a boiling point of 39.5° C., which makes it suitable for these uses.

BACKGROUND OF THE INVENTION

As described above, this invention related to the production of cis-1-chloro-3,3,3-trifluoropropene, which may be designated as HCFO-1233zd (Z), 1233zd(Z), or cis-1233zd. The preferred designation used herein is 1233zd(Z). 1233zd (Z) is a low global warming compound that has applications as a replacement for high global warming materials, for example in foam blowing and aerosol propellant applications.

The isomeric compounds 1233zd may be produced by a number of different methods. Examples include the dehydrochlorination of $CF_3CH_2CHCl_2$ (J. Am. Chem. Soc., 64 (1942) 1157-9); the dehydrofluorination of 3-chloro-1,1,1,3-tetrafluoropropane (U.S. Pat. No. 7,829,747); and the fluorination of halogenated propanes (U.S. Pat. Nos. 5,710,352, 6,111,150, and 6,844,475). Other methods are shown in U.S. Pat. Nos. 6,958,424 and 5,616,819. See also U.S. Patent Pub. No. 2008/0103342 and PCT Pub. No. WO 2010/059496). In most reactions the trans-isomer of 1233zd is the thermal dynamically favored product, with typically only about 3% to 5% of cis-isomer obtained in most manufacturing processes.

PCT Pub. No. WO 2010/068715 provides a process in which the trans-isomer of 1233zd can be isomerized over a fluorinated $Cr_2O_3$ catalyst in the vapor phase at a temperature of about 300° C. The resulting amount of the cis-isomer is only about 10%, combined with from about 2% to 3% of other materials. This process thus requires multiple repeated cycles in order to generate large quantities of the desired cis-isomer of 1233zd.

U.S. Patent Pub. No. U.S. 2012-0215041 A1 (Ser. No. 13/030,789) describes a process for the reduction 1-chloro-3,3,3-trifluoropropyne with palladium under hydrogen atmosphere to stereospecifically generate cis-1233zd in 53% yield. However, unless the reduction process is carefully controlled, over reduction can occur, which leads to the compounds $CF_3CH=CH_2$ and $CF_3CH_2CH_3$.

Both the cis (or Z) isomer and the trans (or E) isomer of 1233zd have practical applications. The cis-isomer of HCFO-1233zd is more suitable for solvent applications than the trans isomer because of a higher boiling point.

U.S. Pat. No. 6,362,383 teaches a process for preparing 1,1,1,3,3-pentafluoro-propane (HFC-245fa) by (1) a first reaction step in which 1,1,1,3,3-pentachloropropane (HCC-240fa) is reacted with hydrogen fluoride in the liquid phase in the presence of a first hydrofluorination catalyst under conditions that are suitable for obtaining a mixture of reaction products comprising 1-chloro-3,3,3-trifluoropropene (HCFO-1233zd) in substantial amount, and (2) a second reaction step in which the 1-chloro-3,3,3-trifluoropropene (HCFO-1233zd) obtained from the first step is reacted with hydrogen fluoride in the liquid phase in the presence of a second hydrofluorination catalyst, and preferably while hydrogen chloride is continuously fed in, in order to obtain 1,1,1,3,3-pentafluoro-propane (HFC-245fa).

The disclosures of the foregoing references are hereby incorporated herein by reference.

Thus there remains a need for a process which makes 1233zd wherein a substantial portion of cis isomer is present or even more preferably, wherein the process stereospecifically produces the cis-isomer of 1233zd.

SUMMARY OF THE INVENTION

The present invention provides a process for the manufacture of cis-1-chloro-3,3,3-trifluoropropene (1233zd (Z)) comprising the treatment of 3,3,3-trifluoropropyne with HCl at a yield of at least about 80%. Preferably the yield of cis-1233zd is at least about 85%. More preferably, the yield is at least about 90%. Most preferably, the yield of cis-1233zd is at least about 95%.

Surprisingly, in the presence of CuCl, the cis-isomer of 1233zd was the predominant reaction product with HCl. The product was essentially pure cis-1233zd with only about 1% to 2% of the trans isomer, which is due to the steric effect in the transition state. In the absence of CuCl (or a similar catalyst) this reaction affords a quantitative yield of 1233zd, but as a mixture of cis and trans isomers.

In certain embodiments, the process uses a solvent in the reaction vessel. In certain embodiments an ionic solvent is used. In certain embodiments the ionic solvent comprises one or more solvents with ammonium ions. Preferred solvents of this type include salts of 1-alkyl-3-methylimidazolium, 1-alkylpyridinium, and N-methyl-N-alkylpyrrolidinium, and mixtures thereof. Especially preferred is a 1-alkyl-3-methyl-imidazolium chloride, such as 1-butyl-3-methyl-imidazolium chloride.

In certain embodiments, a catalyst is used in the reaction vessel. The catalyst may be supported or unsupported. One preferred support for the catalyst comprises activated carbon.

In certain embodiments the catalysts comprise one or more mineral acids. One preferred mineral acid catalyst comprises $H_2SO_4$.

In certain embodiments, the catalyst comprises a Lewis acid or a mixture of Lewis acids. In certain embodiments the Lewis acids comprise metal salts or mixtures thereof. In certain embodiments, the metal salts are selected from the group consisting of copper and antimony and mixtures thereof. In certain preferred embodiments the Lewis acids are selected from the group consisting of CuCl, $CuCl_2$, $SbCl_5$, $ZnCl_2$, $MgCl_2$, $AlCl_3$, $FeCl_3$, and the like ($MCl_x$). Especially preferred is the Lewis acid comprising $CuCl_2$, and more preferably CuCl supported on activated carbon.

In certain embodiments the reaction temperature ranges from 100° C. to 350° C. In certain embodiments the reaction temperature is above 350° C.

In certain embodiments of the reaction the molar ratio of HCl to 3,3,3-trifluoropropyne ranges from about 1:1 to about 3:1. Preferably, the molar ratio of HCl to 3,3,3-trifluoropropyne ranges from about 1.1 to 2.5.

In certain embodiments a carrier gas is employed in the reaction vessel. Preferably the carrier gas is an inert gas. More preferably the inert gas is selected from the group consisting of nitrogen, argon, and mixtures thereof. When a carrier gas is employed, the flow rate ranges from about 20 ml/min to 100 ml/min. In these embodiments the reactants are introduced into the reaction vessel at a flow rate of from about 10 ml/min to 50 ml/min.

In certain embodiments the product of the reaction, namely cis-1-chloro-3,3,3-trifluoropropene, is collected from the reaction vessel in a cooling trap maintained at temperature of from −20° C. to −78° C.

DETAILED DESCRIPTION OF THE INVENTION

As described above, the present invention provides a process for the manufacture of cis-1-chloro-3,3,3-trifluoropropene (1233zd (Z)) comprising the treatment of 3,3,3-trifluoropropyne with HCl.

A variety of ionic solvents can be used for the reaction of 3,3,3-trifluoropropyne with HCl. Examples include salts of 1-alkyl-3-methylimidazolium, 1-alkylpyridinium, N-methyl-N-alkylpyrrolidinium and ammonium ions, or no solvent. An ionic solvent 1-alkyl-3-methylimidazolium chloride, such as 1-butyl-3-methylimidazolium chloride is preferred, with no solvent being most preferred.

As described above, catalysts can be used in this process. These include mineral acids such as $H_2SO_4$ or Lewis acids such as metal salts, especially those of copper and antimony (e.g., $CuCl_2$, CuCl, $SbCl_5$, and the like). Depending on the temperature of the reaction, the catalyst may not be necessary.

Reaction temperatures, for reactions at atmospheric pressure, were limited to 100° C. to 350° C., but the reaction may also proceed at temperatures well above 350° C. To find the appropriate reaction temperature, a pre-mixed 3,3,3-trifluoropropyne and HCl was passed through the heated catalyst/solvent mixture and heating was continued until evidence of reaction was observed (heat release or generation of volatile 1233zd).

The molar ratio of HCl to 3,3,3-trifluoropropyne should be at least one, and can be higher, but ratios in excess of 3 were not particularly advantageous, and might make side-reaction more likely to occur. Molar ratios were typically in the range of 1.1 to 2.5.

In a typical reaction, HCl and 3,3,3-trifluoropropyne were mixed in a stainless cylinder and passed through a mixture of ionic liquid and catalyst or catalyst loaded on activated carbon at 150° C. to 350° C. The carrier gas was typically nitrogen or argon at a speed of 20 to 100 ml/min. The reactants were controlled by a regulating valve at a rate of 10 to 50 ml/min. Product out of the reaction vessel was collected by a cooling trap at temperature of from −20° C. to −78° C.

EXAMPLE 1

14.2 g of 3,3,3-trifluoropropyne and 11.2 g of HCl were mixed in a 150 mL stainless cylinder and passed through a mixture of 11.4 g [Bmim]Cl (1-butyl-3-methyl-imidazolium chloride) and 2.25 g CuCl at 172° C. The product is collected in a −78° C. dry-ice trap followed by −116° C. trap. A total of 4.8 g of products were collected. GC and NMR show 3,3,3-trifluoropropyne and cis-1233zd with 6.8% conversion.

EXAMPLE 2

10.5 g of 3,3,3-trifluoropropyne and 7.1 g of HCl were mixed in a 150 mL stainless cylinder and passed through a mixture of 11.4 g [Bmim]Cl and 2.3 g CuCl at 210° C. The product was collected in a −78° C. dry-ice trap followed by −116° C. trap. A total of 13.5 g of products were collected. GC and NMR showed 3,3,3-trifluoropropyne and cis-1233zd with 17.4% conversion.

EXAMPLE 3

7.3 g of 3,3,3-trifluoropropyne and 5.6 g of HCl were mixed in a 150 mL stainless cylinder and passed through a mixture of 11.2 g [Bmim]Cl and 6.0 g $SbCl_5$ at 180° C. The product was collected in a −78° C. dry-ice trap followed by −116° C. trap. GC and NMR 3,3,3-trifluoropropyne and cis-1233zd with 8.7% conversion.

EXAMPLE 4

The CuCl on activated carbon is made as follows; 3.0 g of cuprous chloride was dissolved in 20 mL of concentrated hydrochloric acid (degassed at 0° C. for 30 min), and the resulting solution was added to 27 g activated carbon under nitrogen, and settled for 2 hours under nitrogen. The mixture was dried under vacuum at 80° C. for 2 hours, then at 100° C. for 16 hours. The obtained catalyst (10% CuCl on carbon) was stored under nitrogen. The activation of catalyst was carried out 300° C. under nitrogen flow of 60 to 100 mL/min for 4 hours before use.

5.4 g of 3,3,3-trifluoropropyne and 4.3 g of HCl were mixed in 75 mL stainless cylinder and passed through the activated CuCl (8 mL, 2.4 g) in 10 mm diameter Monel tube at 300° C. The carrier $N_2$ gas was set at 10 to 20 mL/min, and the feed rate of reactants was 15 to 20 mL/min. Product out of the tube was collected with −78° C. dry-ice trap to give 8.1 g of a mixture with 98.8% yield. GC and NMR showed 3.5% trans-1233zd and 85.3% of cis-1233zd, plus some other unidentified products.

EXAMPLE 5

6.9 g 3,3,3-trifluoropropyne and 5.1 g of HCl were mixed and passed through the catalyst from Example 4 at 300° C. The carrier $N_2$ gas feed rate was set at 25 to 30 mL/min, and the feed rate of the reactant was 5 to 10 mL/min. Product out of the tube was collected with −78° C. dry-ice trap to give 9.3 g of a liquid with 97.1% yield. GC and NMR showed 3.5% trans-1233zd and 87.3% of cis-1233zd, plus some other unidentified products.

EXAMPLE 6

4.8 g 3,3,3-trifluoropropyne and 4.0 g of HCl were mixed and passed through the catalyst from Example 5 at 250° C. The carrier $N_2$ gas feed rate was set at 25 to 30 mL/min, and the feed rate of the reactant was 10 to 15 mL/min. Product out of the tube was collected with a −78° C. dry-ice trap to give 6.5 g of a mixture with 97.6% yield. NMR showed 1.8% trans-1233zd and 97.6% of cis-1233zd.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A process for making cis-1-chloro-3,3,3-trifluoropropene comprising reacting 3,3,3-trifluoropropyne with HCl and a Lewis acid comprising CuCl in a reaction vessel at a yield of at least about 80%.

2. The process of claim 1, wherein a solvent is used in the reaction vessel.

3. The process of claim 2, wherein the solvent comprises an ionic solvent.

4. The process of claim 3, wherein the ionic solvent comprises one or more solvents with ammonium ions.

5. The process of claim 4, wherein the ionic solvent is selected from the group consisting of salts of 1-alkyl-3-methylimidazolium, 1-alkylpyridinium, and N-methyl-N-alkylpyrrolidinium, and mixtures thereof.

6. The process of claim 4, wherein the ionic solvent comprises 1-butyl-3-methylimidazolium chloride.

7. The process of claim 1, wherein a catalyst is used in the reaction vessel.

8. The process of claim 7, wherein the catalyst is on a support.

9. The process of claim 8, wherein the catalyst support comprises activated carbon.

10. The process of claim 7, wherein the catalyst further comprises one or more mineral acids.

11. The process of claim 10, wherein the mineral acid comprises $H_2SO_4$.

12. The process of claim 7, wherein the catalyst further comprises a mixture of Lewis acids.

13. The process of claim 12, wherein the Lewis acids comprises metal salts or mixtures thereof.

14. The process of claim 13, wherein the metal salts are selected from the group consisting of copper and antimony and mixtures thereof.

15. The process of claim 12, wherein the Lewis acid is selected from the group consisting of $CuCl_2$, $SbCl_5$, $ZnCl_2$, $MgCl_2$, $AlCl_3$, $FeCl_3$, and the like ($MCl_x$)).

16. The process of claim 1, wherein the CuCl is supported on activated carbon.

17. The process of claim 1, wherein the reaction temperature ranges from 100° C. to 350° C.

18. The process of claim 1, wherein the reaction temperature is above 350° C.

19. The process of claim 1, wherein the molar ratio of HCl to 3,3,3-trifluoro-propyne ranges from about 1:1 to about 3:1.

20. The process of claim 19, wherein the molar ratio of HCl to 3,3,3-trifluoro-propyne ranges from about 1.1 to 2.5.

21. The process of claim 1, wherein a carrier gas is employed in the reaction vessel.

22. The process of claim 21, wherein the carrier gas is an inert gas.

23. The process of claim 22, wherein the inert gas is selected from the group consisting of nitrogen, argon, and mixtures thereof.

24. The process of claim 21, wherein the carrier gas is used at a flow rate of from about 20 mL/min. to 100 mL/min.

25. The process of claim 22, wherein the reactants are introduced into the reaction vessel at a flow rate of from about 10 mL/min. to 50 mL/min.

26. The process of claim 1, wherein the cis-1-chloro-3,3,3-trifluoropropene is collected from the reaction vessel in a cooling trap maintained at temperature of from −20° C. to −78° C.

* * * * *